United States Patent
Waxler

(10) Patent No.: US 7,024,454 B1
(45) Date of Patent: Apr. 4, 2006

(54) WORK SHARING AND COMMUNICATING IN A WEB SITE SYSTEM

(75) Inventor: Andrea Waxler, Andover, MA (US)

(73) Assignee: Practicefirst.com L.L.C., Foxboro, MA (US)

( * ) Notice: Subject to any disclaimer, the term of this patent is extended or adjusted under 35 U.S.C. 154(b) by 823 days.

(21) Appl. No.: 09/648,473

(22) Filed: Aug. 25, 2000

(51) Int. Cl.
*G06F 15/16* (2006.01)

(52) U.S. Cl. ............... 709/204; 709/203; 709/205; 709/213; 709/223; 709/246

(58) Field of Classification Search ........... 709/203, 709/204, 205, 213, 223, 246
See application file for complete search history.

(56) References Cited

U.S. PATENT DOCUMENTS

| | | | |
|---|---|---|---|
| 5,799,318 A | | 8/1998 | Cardinal et al. |
| 5,832,497 A | * | 11/1998 | Taylor ................... 707/104.1 |
| 5,848,412 A | * | 12/1998 | Rowland et al. ............ 707/9 |
| 5,889,952 A | | 3/1999 | Hunnicutt et al. |
| 5,913,032 A | * | 6/1999 | Schwartz et al. ........... 709/213 |
| 6,014,135 A | * | 1/2000 | Fernandes ................. 345/744 |
| 6,016,478 A | * | 1/2000 | Zhang et al. ................. 705/9 |
| 6,038,601 A | | 3/2000 | Lambert et al. |
| 6,182,117 B1 | * | 1/2001 | Christie et al. ............. 709/205 |
| 6,195,641 B1 | * | 2/2001 | Loring et al. .............. 704/275 |
| 6,216,169 B1 | * | 4/2001 | Booman et al. ............ 709/246 |
| 6,236,994 B1 | * | 5/2001 | Swartz et al. ................. 707/6 |
| 6,256,664 B1 | * | 7/2001 | Donoho et al. ............. 709/204 |
| 6,366,956 B1 | * | 4/2002 | Krishnan .................... 709/223 |
| 6,442,693 B1 | * | 8/2002 | Sandgren et al. ........... 713/200 |
| 6,446,113 B1 | * | 9/2002 | Ozzie et al. ................. 709/204 |
| 6,463,447 B1 | * | 10/2002 | Marks et al. ................ 715/513 |
| 6,842,774 B1 | * | 1/2005 | Piccioni ..................... 709/207 |
| 2001/0034701 A1 | * | 10/2001 | Fox et al. ..................... 705/38 |

* cited by examiner

*Primary Examiner*—Nabil El-Hady
(74) *Attorney, Agent, or Firm*—Fish & Richardson P.C.

(57) ABSTRACT

Disclosed is a method and apparatus for work sharing and communicating in a service oriented industry. A web site system that includes a communication component and a data storage component allows users to electronically input data. The method and apparatus then electronically store the inputted data in the storage component, automatically determine to which other related portions of the web site system the data will be sent, and distribute the data to those determined portions. There, the data is stored in the data storage component, and a communication is sent the users of the relevant portions of the web site to notify them of the newly stored data.

13 Claims, 2 Drawing Sheets

WORK SHARING AND COMMUNICATING IN A WEB SITE SYSTEM

The invention relates to work sharing and communicating over the internet. More particularly, the invention relates to exchanging information with professionals over the internet and storing such information at a location remote from that of the professional.

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO MATERIAL ON A COMPACT DISC

Applicant incorporates by reference the material on the compact disc Practicfirst.com having the following files:

| Name | Size | Type | Date Created |
|---|---|---|---|
| ClinicalProcedures.nsf | 820 KB | NSF | Aug. 17, 2000 |
| CodingDiscussion.nsf | 1,170 KB | NSF | Aug. 17, 2000 |
| CoporatedDocLibrary.nsf | 923 KB | NSF | Aug. 17, 2000 |
| DocLibrary.nsf | 1,170 KB | NSF | Aug. 17, 2000 |
| FinancialReporting.nsf | 3,840 KB | NSF | Aug. 21, 2000 |
| FirstPracticeToDo.nsf | 6,656 KB | NSF | Aug. 17, 2000 |
| GoveringPolicies.nsf | 923 KB | NSF | Aug. 17, 2000 |
| ManagerDiscussion.nsf | 1,040 KB | NSF | Aug. 7, 2000 |
| MDDiscussion.nsf | 1,170 KB | NSF | Aug. 17, 2000 |
| MedicalPolicies.nsf | 923 KB | NSF | Aug. 17, 2000 |
| OfficePolicies.nsf | 1,040 KB | NSF | Aug. 21, 2000 |
| OfficeProcedures.nsf | 923 KB | NSF | Aug. 21, 2000 |
| PersonnelPolicies.nsf | 1,170 KB | NSF | Aug. 17, 2000 |
| pfirst.nsf | 6,400 KB | NSF | Aug. 20, 2000 |
| StaffDiscussion.nsf | 1,170 KB | NSF | Aug. 15, 2000 |

BACKGROUND OF THE INVENTION

In many service businesses, hard-copy paper files and/or computer systems having terminals intercoupled over a private network contain, store, and organize the information needed for day-to-day business operations.

It is an important object of the invention to provide improved information storage and retrieval for professionals.

BRIEF SUMMARY OF THE INVENTION

According to the invention, work sharing and communicating comprises a web site system that includes at least a communication component and a data storage component allowing users to electronically input data over the internet. The inputted data may be electronically stored in the data storage component. The web site system then automatically determines to which other related portions of the web site system (i.e., billing, calendar, etc.) the data will be sent. The data is then automatically distributed to those determined portions. There, the data is stored in the data storage component, and a communication (i.e., an email) is sent over the internet to the users of the relevant portions of the web site to notify them of the newly stored data.

In several aspects of the invention, the system includes a computer program, programmed to determine which portions of the web site system the electronically stored data will be sent, that automatically determines which portions are relevant. It receives the electronically stored data, processes to which portions of the web site system the electronically stored data is relevant, and enacts the automatic distribution to distribute the electronically stored data accordingly.

In an embodiment of the invention, an apparatus for work sharing and communicating comprises a computer for providing a web site system that includes at least a communication component and a data storage component, allowing users to electronically input data over the internet from remote locations. The inputted data is stored in a data storage device (i.e., a centralized mainframe), and then a computer program automatically determines to which other related portions of the web site system (i.e., billing, calendar, etc.) the electronically stored data will be sent. Another computer program then automatically distributes the electronically stored data to the automatically determined other related portions of the web site system. There, a data storage device electronically stores the data distributed to the other related portions of the web site system. A computer program, such as an email program, automatically communicates over the internet to other relevant users of the newly stored data in the web site system.

An embodiment of the invention is a method for enrolling and grouping users. Users who enroll into the web-based system are assigned specific work groups. Each work group has different levels of access to the web site system. Depending on a user's level of access, they are provided with specific communication capabilities specific to their work group.

An embodiment of the invention is a method for enrolling users into an intranet/extranet web site system. Initially, the web site prompts users to input business information, number of users, and size of the organization over the internet. Once they input this information, it is stored in a storage component of the web site system. The web site system then prompts the user for credit card information, stores it in a storage component of the web site system, and validates it. Once validated, the web site system prompts the user for input of a username, password, and a group which are then stored in a storage component of the web site system. The web site system replicates the intranet from the server for use by the user.

The invention has many advantages. For example, the knowledge management web-site system provides the functionality of business applications (i.e., organizing, maintaining, and updating data) with many added features. Work sharing capability is automated and expedited, as is data storage and archival. Another advantage is increased communication by automatic email messages, calendar updates, and memorandum postings. The invention also provides for rapid, automatic integration of multi-departmental businesses by automatic interdepartmental communication, automatic data storage, and automatic data retrieval.

The web site system is also remotely accessible, meaning that businesses are not limited to site-dependant networks. Site independence liberates service businesses from having to return to a specific site to integrate data obtained outside the site. Storing information remotely, businesses need not own or maintain hardware and software. Businesses can function in a virtual office environment. This allows for them to be more accessible at a discounted cost. Since the web site system has both intranet and extranet capabilities, it requires very little personal support to maintain the web-based system.

The invention also has the advantage of saving employee time. When one employee enters data, it will be automatically sent to all other relevant employees. Co-workers need not spend time hunting down data. Very little employee time is spent maintaining, servicing, updating, organizing, transferring, and simply finding data. Furthermore, data and files are less susceptible to loss, disorganization, and a lack of maintenance and updates.

The web site system also provides pre-established, department specific and geographic specific links that are easily accessible and are all maintained in single environment in appropriate functional areas. For example, a payroll work group portion of a business in a given state may have payroll specific links to payroll companies in that state, and a banking portion may have links to specific banks in the proximate geographic region.

Other advantages of the invention follow from the features, objects and following detailed description when read in connection with the accompanying drawings.

DETAILED DESCRIPTION OF THE INVENTION

Figure 1:
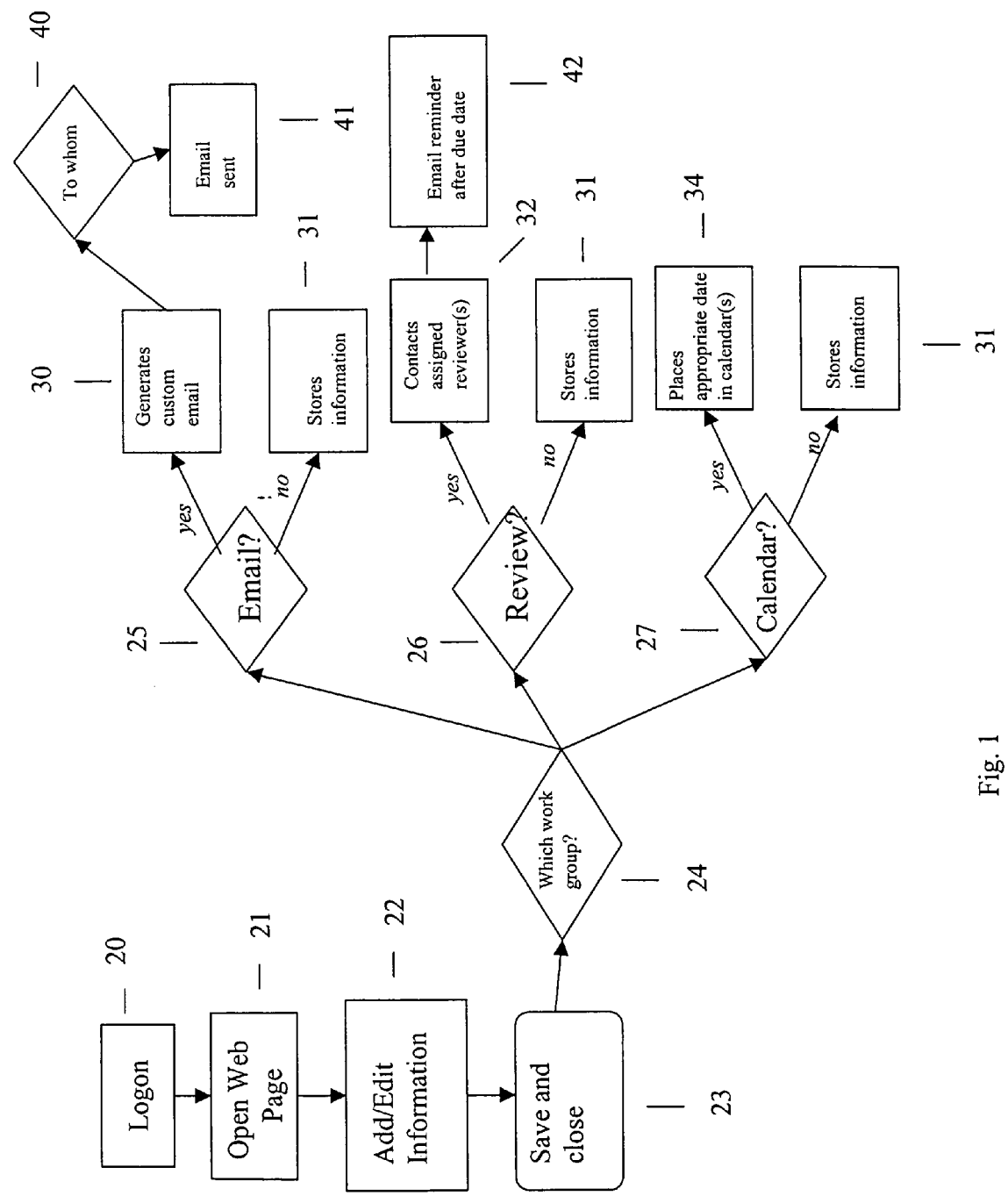
FIG. 1 is a block diagram of a process flow management system implemented in a web site system for management and control of workflow process activities performed by the users of the web site system according to the invention.

FIG. 1 shows a block diagram of a workflow knowledge management and communication web site system 10 that operates in accordance with the present invention. In an exemplary embodiment of the invention, a medical practice uses the web site system to run its day-to-day operations. A user, such as a physician, logs on to the web site system at step 20 by typing in a URL address into a computer that is connected to the internet. A web page 21 appears and prompts the user to add or edit information at step 22. The user then adds or edits information as requested. This information is saved by the web site system 10 in step 23 and the screen is closed.

Step 24 depicts the web site system 10 then automatically determining to which work group within the intranet, specific to the medical practice, the added or edited information of step 22 relates. For example, the user is a physician. The physician calls a patient from his home. He records a transcript of the conversation and adds it as new information in step 22. After the transcribed conversation is saved and the screen closed, the web site system 10 automatically determines that the information should be passed to the work group "medical records" in step 24. Once the web site system 10 determines to which work group information should be conveyed, it then automatically determines which of several steps need be enacted to convey the information appropriately.

Step 25 illustrates the web site system 10 automatically determining whether an email should be sent to the determined work group of step 24. If it determines that and email should be sent, the web site system 10 automatically generates a custom email specifically tailored for the information added and for the determined work group in step 30. Returning to the example above, the web site system 10 determines that the medical records group should receive an email in step 25. It then automatically generates an email, as per step 30, which includes the physician's transcribed conversation, the physician's name, the time the call was taken, and a message requesting the medical records group to print and file the transcript in the patient's chart. In step 40, the web site system 10 automatically determines to whom the email generated in step 30 should be sent. It also automatically determines whether a response email is needed and indicates as such in the generated email. The web site system 10 automatically sends the email in step 41 to the users determined in step 40. If, in step 25, the web site system 10 determines that no email should be sent, it stores the information in a data storage component in step 31.

Step 26 illustrates the web site system 10 automatically determining whether a review policy need be added or altered. In a medical practice often policies such as office policies, medical policies, and personnel policies are enacted to ensure that proper procedures are in place. If information is added or edited in step 22 that affects these policies, once a work group or work groups are selected, the web site automatically determines if a review of policy change or new policy is necessary in step 26. If the answer is yes, step 32 illustrates web site system 10 automatically assigning relevant contacts a reviewer or reviewers. The reviewer can consist of an entire work group, or any number of individual members thereof. Once these reviewers are assigned, web site system 10 will automatically email them review reminders after the due date of the review in step 42. If, in step 26, the web site system 10 determines that no review is necessary, it stores the information in a data storage component in step 31.

Step 27 illustrates the web site system 10 automatically determining whether a calendar update in a calendar program need be added or altered. If, for example, web site system 10 determines that a review is necessary in step 26, it will then automatically determine that a calendar update need be made in the appropriate individuals' calendar programs that are assigned to perform the review. This determination is illustrated by step 27. In step 34, web site system 10 will automatically place a notation on the appropriate date in the reviewer's or reviewers' calendars. If, in step 27, the web site system 10 determines that no calendar update is necessary, it stores the information in a data storage component in step 31.

Figure 2:
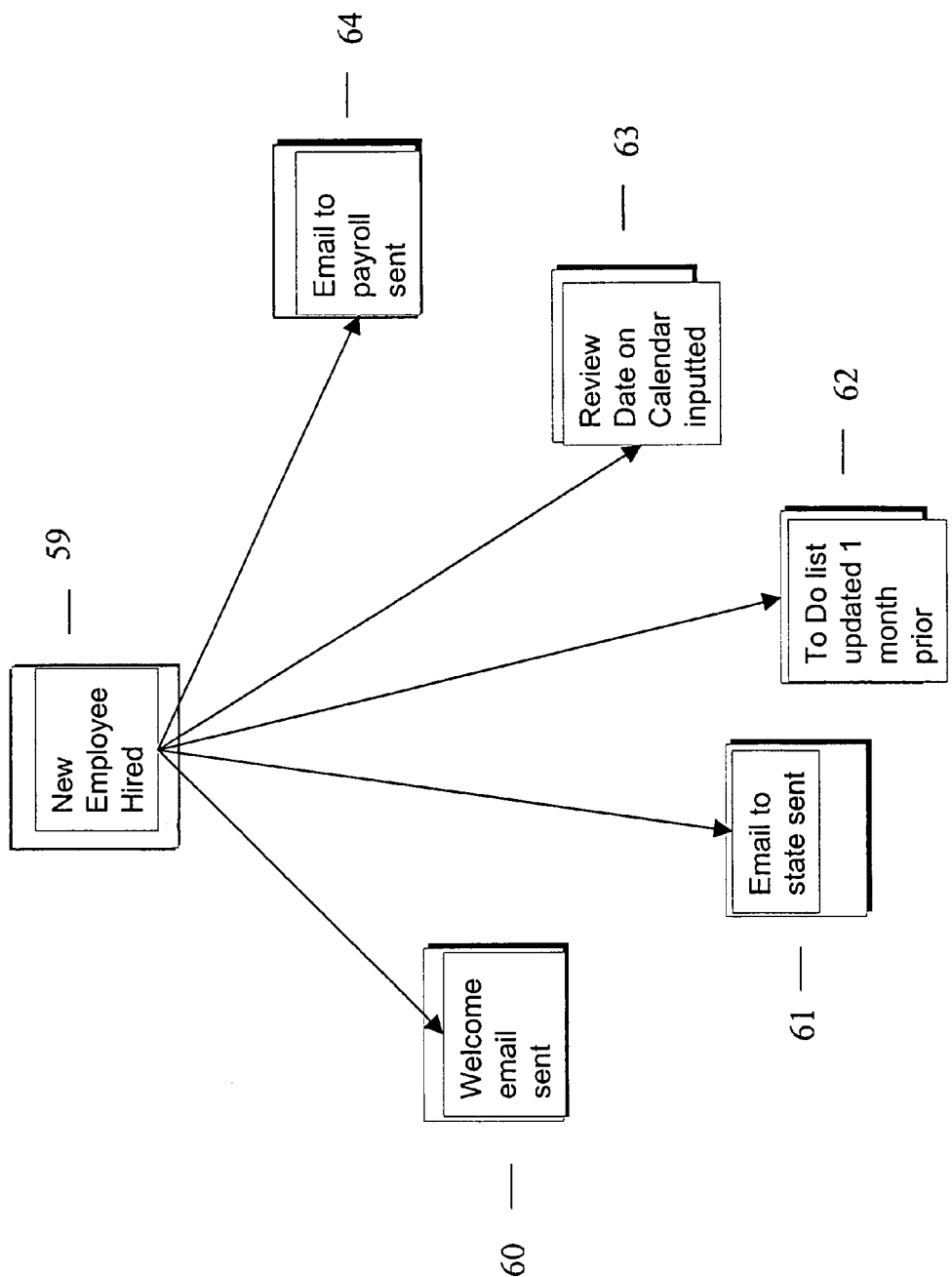
FIG. 2 is a flow diagram illustrating automatic determination, distribution, and communication steps of the invention.

FIG. 2 shows a flow diagram of the automatic steps taken when a new employee is hired 59, and information is entered into the web site system 10. Referring to FIG. 1, Web site system 10 automatically selects all work groups in step 24 when a user enters a new employee's information. The invention automatically sends an email 60 to every user in the intranet, introducing and welcoming the new employee. Web site system 10 also automatically sends an email 61 to the proper state and federal employment and taxation agencies conveying necessary taxation and employment information. Web site system 10 further automatically updates manager of the new employee's to do list 62 and calendar 63, effectively scheduling a review date and reminder of the employee's review. An email 64 is also sent to the payroll department informing them to begin processing the new employee's payments.

There is enclosed a CD-ROM with software entered at the remote site along with Lotus R5 software commercially available from Lotus Corporation of an exemplary embodiment of the invention for physicians offices.

It is evident that . . . those skilled in the art may no make numerous uses of and departures from the specific apparatus and techniques disclosed herein without departing from the inventive concepts. Consequently, the invention is to be construed as limited only by the spirit and scope of the appended claims.

What is claimed is:

1. A method of work sharing and communicating over the internet with a web site system that includes at least a communication component and a data storage component allowing users in professional offices to electronically input data over the internet comprising, electronically storing the data received over the internet in the data storage component of the web site system;

automatically determining to which other related portions of the web site system the electronically stored data will be sent;

automatically distributing the electronically stored data to the automatically determined other related portions of the web site system;

electronically storing the data distributed to the other related portions of the web site system in the data storage component; and automatically communicating over the internet to other relevant users of the newly stored data in the web site system.

2. The method of claim 1, wherein said automatically determining is controlled by a computer program programmed to determine which portions of the web site system the electronically stored data will be sent.

3. The method of claim 2, wherein the computer program controls determining to which portions of the web site system the electronically stored data is relevant, and enacts the automatic distribution to distribute the electronically stored data accordingly.

4. The method of claim 3 wherein the portions of the web site system further comprise portions of a knowledge-management system.

5. The method of claim 4 wherein the knowledge-management system further comprises a service industry knowledge management system.

6. The method of claim 5, wherein the service industry is from the group consisting of a medical practice, hospital, and a medical health maintenance organization.

7. The method of claim 5, wherein the service industry is from the group consisting of a law office, law firm, courthouse, and a legal business entity.

8. The method of claim 5, wherein the service industry is from the group consisting of an accounting firm, tax firm, temporary employment firm, financial and employment business entity.

9. The method of claim 1, wherein the electronic storage occurs on a remote data processing machine that can be accessed from remote terminals via a channel from the group consisting of the internet and an intranet.

10. The method of claim 1, wherein the automatic distributing is controlled by a computer program programmed to distribute the electronically stored data to the automatically determined portions of the web site system.

11. An apparatus for work sharing and communicating comprising:

a computer at a web site system that includes at least a communication component and a data storage component allowing users in professional offices to electronically input data over the internet;

a data storage device for electronically storing the data electronically inputted into the web site system;

a source of a computer program for automatically determining to which other related portions of the web site system the electronically stored data will be sent;

a source of a computer program for automatically distributing the electronically stored data to the automatically determined other related portions of the web site system;

a data storage device for electronically storing the data distributed to the other related portions of the web site system; and a source of a computer program for automatically communicating over the internet to other relevant users of the newly stored data in the web site system.

12. The apparatus of claim 11, wherein the web site system includes terminals intercoupled to the computer by a link.

13. The apparatus of claim 11 wherein the data storage comprises data storage device that stores the first input data and a data storage device that stores the data distributed to the other related portions of the web site system.

* * * * *